United States Patent [19]

England et al.

[11] 4,316,986

[45] Feb. 23, 1982

[54] PREPARATION OF DIFLUOROMALONYL FLUORIDE

[75] Inventors: David C. England, Wilmington; Robert L. Kraft, Newark; Carl G. Krespan, Wilmington, all of Del.

[73] Assignee: E. I. DuPont de Nemours & Company, Wilmington, Del.

[21] Appl. No.: 189,827

[22] Filed: Sep. 23, 1980

[51] Int. Cl.³ .............................................. C07C 67/14
[52] U.S. Cl. .................... 560/184; 260/544 F; 560/62; 560/105; 560/192; 560/227
[58] Field of Search ............... 560/192, 62, 105, 184, 560/227; 260/544 F

[56] References Cited

U.S. PATENT DOCUMENTS

| | | | |
|---|---|---|---|
| 3,250,807 | 5/1966 | Fritz et al. | 260/535 |
| 3,557,165 | 1/1971 | Dorfman et al. | 260/404 |
| 3,948,761 | 4/1976 | Siskin | 208/134 |
| 4,122,115 | 10/1978 | Middleton | 260/544 |
| 4,127,731 | 11/1978 | Yamabe et al. | 560/192 |
| 4,131,740 | 12/1978 | England | 560/180 |
| 4,151,200 | 4/1979 | Yamabe et al. | 260/544 |
| 4,154,753 | 5/1979 | Fielding | 260/544 F |
| 4,201,876 | 5/1980 | Griffin | 260/544 F |
| 4,247,713 | 1/1981 | England | 560/192 |

FOREIGN PATENT DOCUMENTS 53-40708  9/1976  Japan.
53-111011  3/1977  Japan.

OTHER PUBLICATIONS

Fear et al., in J. Appl. Chem., 5, 589 (1955).
Fawcett et al., in J. Amer. Chem. Soc., 84, 4280 (1962).
Lovelace et al., in "Aliphatic Fluoride Compounds", ACS Monograph Series No. 138, 219 to 228 (1958).
Hudlicky, in "Chemistry of Organic Fluoride Compounds", Mac Millen, 151 (1961).
Olah et al., in Science, 206 (4414), 13 (1979).
Howells and McCown, Chem. Revs. 77 (1), 69 (1977).
Yakobson and Furin, Synthesis, 1980 (5), 345.
England et al., J. Fluorine Chem., 3, 63, 1973.
Lovelace et al., "Aliphatic Fluorine Compounds", Reinhold, 1958, pp. 2, 7 to 10.
Olah at al., "Advances in Fluorine Chemistry", 7, 69, 1973.
Krespan et al., "Fluorine Chemistry Reviews", 1, 147, 1967.

*Primary Examiner*—Natalie Trousof
*Assistant Examiner*—Vera C. Clarke
*Attorney, Agent, or Firm*—James A. Costello

[57] ABSTRACT

Carboxylic ester and acyl fluoride groups are interchanged in the presence of a metal fluoride catalyst or a metal fluoride/strong sulfonic acid catalyst combination to produce fluorinated mono- and diacyl fluorides.

10 Claims, No Drawings

PREPARATION OF DIFLUOROMALONYL FLUORIDE

BACKGROUND OF THE INVENTION

This invention concerns a catalyzed carboxylic ester-/acyl fluoride interchange reaction as a route to fluorinated mono- and diacyl fluorides.

Nothing found in the prior art discloses an interchange reaction of the type herein disclosed as a route to preparation of fluorinated mono- and diacyl fluorides. Typical prior art processes include the following: U.S. Pat. No. 4,151,200 discloses preparation of polyfluorodiacyl fluorides by reaction of perfluorolactone with a fluorocarbon epoxide such as hexafluoropropene oxide; Japanese Application 53/111,011 discloses preparation of polyfluorodiacyl fluorides by reaction of an α,ω-diiodopolyfluoroalkane with $SO_3$; Japanese Application No. 53/040,708 discloses preparation of fluorinated ester-acyl fluorides from diacyl fluorides; U.S. Pat. No. 3,250,807 discloses preparation of diacyl fluorides of fluorocarbon ethers by reaction of a perfluroinated diacyl fluoride such as oxalyl fluoride or difluoromalonyl fluoride with hexafluoropropene oxide.

In addition, U.S. patent application Ser. No. 071,684, now abandoned, discloses preparation of difluoromalonyl fluoride by reacting 3-methoxytetrafluoropropionyl fluoride with $TiF_4$ or $SbF_5$. Fear et al., in J. Appl. Chem., 5, 589 (1955), describe preparation of difluoromalonic acid and its reaction with phosphorus oxychloride to give difluoromalonyl chloride.

Fawcett et al, in J. Amer. Chem. Soc., 84, 4280 (1962), disclose preparation of 3-methoxy tetrafluoropropionyl fluoride from methyl trifluorovinyl ether by reaction with carbonyl fluoride; Lovelace et al, in "Aliphatic Fluoride Compounds", ACS Monograph Series No. 138, 219 to 228 (1958) and Hudlicky, in "Chemistry of Organic Fluoride Compounds", MacMillan, 151 (1961), disclose several methods of preparing fluorinated monoacyl fluorides, most commonly by heating the corresponding acyl chlorides with a metal fluoride such as KF or $SbF_3$.

Olah, et al., in Science, 206 (4414), 13 (1979), describe the addition of hydrofluoric or fluorosulfonic acids to the known Lewis acid fluorides; $SbF_5$, $TaF_5$, $NbF_5$, $AsF_5$ or $BF_3$, especially $SbF_5$, to produce "superacid" systems of high catalytic activity. Highest acidity is said to be achieved in the $HF-SbF_5$ system.

Howells and McCown, Chem. Revs., 77 (1), 69 (1977); and Yakobson and Furin, Synthesis, 1980 (5), 345, also describe highly acidic catalytic mixtures of fluorosulfonic or hydrofluoric acids with $SbF_5$; highest acidity is ascribed to the $HSO_3F-SbF_5$ system. Howells and McCown also disclose highly acidic mixtures of $SbF_5$ or $TaF_5$ with trifluoromethane sulfonic acid.

SUMMARY OF THE INVENTION

This invention concerns the following reaction process:

$RX-CO_2CH_3 + R'X'-COF$ 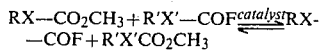 $RX-COF + R'X'CO_2CH_3$ wherein

X is methylene or substituted methylene selected from $-CF_2-$, $-CFH-$, $-CFCl-$, $-CFBr-$, $-CFI-$, and $-C(CF_3)F-$;

X' is substituted methylene selected from $-CF_2-$, $-CFH-$, $-CFCl-$, $-CFBr-$, $-CFI-$ and $-C(CF_3)F-$;

R and R' are the same or different and are selected from hydrogen, halogen, and halogen-substituted and unsubstituted alkyl, alkoxy, alkaryl, aralkyl, aryloxy and polyether alkyl of up to 18 carbon atoms;

R and X taken together can be $R_FCOF$;

R' and X' taken together can be $R_FCO_2CH_3$; and $R_F$ is a single bond or a linear or branched perfluoroalkylene group of up to 18 carbon atoms.

Preferred compositions are those wherein X is $-CF_2-$, $-CFH-$ or $-CFCl-$; R is hydrogen, fluorine or perfluoroalkyl; X' is $-CF_2-$ or $-C(CF_3)F-$; R' is $CF_3CF_2CF_2O(CF(CF_3)CF_2O)_n$ wherein n is 0 to 10; R and X taken together are $R_FCOF$; R' and X' taken together are $R_FCO_2CH_3$; and $R_F$ is $-CF_2-$.

DETAILS OF THE INVENTION

Useful catalysts include one or more metal fluorides selected from the group $SbF_5$, $TaF_5$, $NbF_5$, $AsF_5$, $BiF_5$, $TiF_4$, $ZrF_4$, and mixtures of $SbF_5$ and hydrofluoric acid (HF) wherein $HSbF_6$ is present; as well as one or more of such metal fluorides in combination with one or more strong sulfonic acid(s) (sometimes called superacids) such as fluorosulfonic acid, trifluoromethanesulfonic acid, and perfluorosulfonic acid resin such as Nafion ®. The metal containing catalysts are employed in an amount such that about 0.01 to 1.0 mol, preferably 0.05 to 0.5 mol of metal per mol of starting acyl fluoride is present.

Preferred catalysts are the mixtures of hydrofluoric acid or strong sulfonic acid(s) with the metal fluoride(s). The preferred catalysts produce higher yields of products than do the metal fluorides alone. An especially preferred combination is fluorosulfonic acid with $SbF_5$. Typically, the combination catalysts comprise about 50 to 95 mol percent of sulfonic acid(s) and about 5 to 50 mol percent of metal fluoride(s). Preferably, the combination catalysts comprise about 70 to 90 mol percent of sulfonic acid(s) and about 10 to 30 mol percent of metal fluoride(s). It is believed that HF, and the sulfonic acids employed in somewhat greater than catalytic amounts, serve as strong proton sources, said protons enhancing the catalytic activity of the metal fluoride. Nevertheless, the acids will still be employed within the defined ratios relative to metal fluoride.

It will be appreciated that the generic reaction sequence depicted above encompasses the subgeneric reaction:

$2FOC-R_F-CO_2CH_3$ 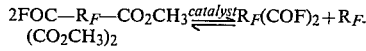 $R_F(COF)_2 + R_F(CO_2CH_3)_2$ wherein $R_F$ is a single bond or a linear or branched perfluoroalkylene group of up to 18 carbon atoms.

To prepare a given monoacyl fluoride, RX—COF, the corresponding methyl ester, $RXCO_2CH_3$, is reacted with another monoacyl fluoride in the presence of a catalyst. The starting acyl fluoride, R'X'COF, will normally by an available, relatively low-cost, "sacrificial" compound. Suitable "sacrificial" acyl fluorides are oligomers of hexafluoropropene oxide (HFPO) of the formula

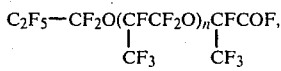

where n is 0 to 10, prepared by fluoride ion-catalyzed polymerization of HFPO. Said oligomers generally have higher boiling points than the acyl fluoride products, RX—COF. It is desirable that the product acyl fluoride have a lower boiling point than that of either reactant so that it can be continuously removed by distillation during the reaction, thus helping to drive the reaction in the direction of RX—COF formation.

The starting methyl ester, RX—CO$_2$CH$_3$, and starting acyl fluoride, R'X'COF, are normally combined in the molar ratio of about 1:1 to 1:10, preferably about 1:1 to 1:1.3, i.e., with the acyl fluoride in slight excess. This reaction can be employed to prepare nonfluorinated acyl fluorides, such as acetyl fluoride, but higher yields are normally obtained when both X and X' groups adjacent to —CO$_2$CH$_3$ and —COF—, respectively, contain at least one fluorine atom.

In preparing diacyl fluorides, R$_F$(COF)$_2$, a fluorinated α-carboxylate-ω-acyl fluoride reactant, FOCR$_F$CO$_2$CH$_3$, preferably higher boiling than the diacyl fluoride product, is employed without a second ester or acyl fluoride.

In general, reaction temperatures are about 0° to 200° C., preferably 20° to 100° C. Preferred reaction temperatures are at the boiling point of the lower boiling reactant, in the embodiments of the invention employing two reactants. In the embodiment wherein the ester/acyl fluoride, FOCR$_F$CO$_2$CH$_3$, is the sole reactant, the preferred reaction temperature is its boiling point. Pressure is not critical, and pressures both below and above atmospheric pressure and operable; pressures close to atmospheric are preferred. Halogenated diluents such as Freon® E3, a commercial product of the formula F[CF(CF$_3$)CF$_2$O]$_3$CHFCF$_3$, or Freon® 113 (1,1,2-trichlorotrifluoroethane) can be employed but are generally unnecessary.

The mono- and diacyl fluorides prepared by the process of this invention are useful intermediates for organic synthesis and some have specialized utility. For example, perfluorinated diacyl fluorides are initiators for the polymerization and copolymerization of hexafluoropropene oxide. Monoacyl fluorides containing perfluoro-2-methyl acetyl fluoride end groups, —CF(CF$_3$)COF, can be pyrolyzed to vinyl monomers.

The following Examples illustrate the invention. Parts are by weight unless otherwise noted. Preferred embodiments are those of Examples 3, 5 and 6.

EXAMPLE 1

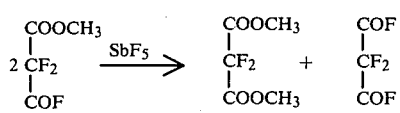

A mixture of 69.3 g (0.44 mol) of methyl difluorofluoroformyl acetate and 18.8 g (0.08 mol) of SbF$_5$ was refluxed for 11 hrs in a flask with a water-cooled condenser having a Dry Ice-cooled trap attached to the condenser. Material which collected in the trap (10.5 g) was distilled in a low temperature still to give about 4.6 g of difluoromalonyl fluoride, b.p. −9°, and 1 g of by-product methyl trifluoroacetate, b.p. 46°. Material which remained in the reaction flask was distilled to give a small amount of dimethyl difluoromalonate, 41 g of reactant, and about 4 grams of methyl trifluoroacetate.

EXAMPLE 2

To 69.5 g (0.45 mol) of methyl difluorofluoroformylacetate was added premixed (cold) SbF$_5$ (16.6 g, 0.08 mol) and HF (1.4 g, 0.07 mol), equivalent to 18.0 g (0.08 mol) of HSbF$_6$. In the manner of Example 1, this mixture was refluxed for 11 hrs. Distillation of material which collected in the Dry Ice trap (16.5 g) gave about 12 g of difluoromalonyl fluoride. Distillation of the material remaining in the reaction flask gave 12.7 mg of dimethyl difluoromalonate, 30 g of reactant, and about 1.2 g of methyl trifluoracetate.

EXAMPLE 3

A mixture of 84 g (0.54 mol) of methyl difluorofluoroformylacetate, 104 g (1.0 mol) of fluorosulfonic acid and 9 g (0.038 mol) of HSbF$_6$ was heated at 100° to 115° for 20 h. Then, 25.6 g of volatile product, collected through a condenser in a −80° trap, and boiling in the range of −25° to +10°, was identified by IR as difluoromalonyl fluoride (66% yield) based on the stoichiometry 2 FOCCF$_2$CO$_2$CH$_3$:CF$_2$(COF)$_2$. Dimethyl difluoromalonate was also formed.

EXAMPLE 4

A mixture of 624 g (4.0 mol) of methyl difluorofluoroformylacetate, 348 g (3.5 mol) of fluorosulfonic acid and 25 ml of HSbF$_6$ (0.3 mol) was charged to a 1 liter Teflon® pot fitted with a Teflon® condenser connected to a trap cooled to −80°. The mixture was stirred and heated at 80° to 110° for about 24 h. Then, 187 g (65% yield) of crude difluoromalonyl fluoride was collected which, after trap-to-trap distillation, was analyzed by NMR at −30°. NMR (CCl$_4$): $^{19}$F 21.0 (t, $J_{FF}$ 10.9 Hz, 2F, COF) and −112.4 ppm (t, $J_{FF}$ 10.9 Hz, 2F, CF$_2$) with a very small amount of impurity showing at −162.1 ppm. Distillation of a 140 g sample gave 118 g of pure FCOCF$_2$COF, b.p. −4° to −5°. Dimethyl difluoromalonate was also formed.

EXAMPLE 5

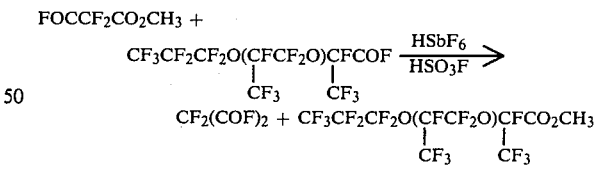

The pot residue from Example 4 was treated with 187 g (0.38 mol) of hexafluoropropene oxide (HFPO) trimer, b.p. 84° (330 mm). Evolution of product resumed at 90°, and the reaction mixture was stirred and heated slowly to 100° over 20 h. Further heating to 105° had little effect. Product isolated by trap-to-trap distillation was 20 g (40% yield) of FCOCF$_2$COF, identified by IR. The methyl ester of HFPO trimer was also formed.

EXAMPLE 6

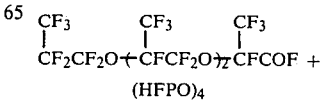

-continued

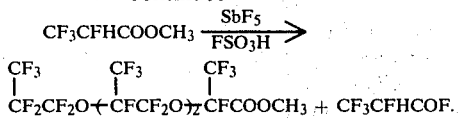

$$CF_2CF_2O\!+\!CFCF_2O\!\!\!\!\!\!\!\!\rightarrow_{\overline{n}}\!CFCOOCH_3 + CF_3CFHCOF.$$

A mixture of 32 g (0.2 mol) of CF₃CFHCOOCH₃, 172 g (0.26 mol) of HFPO tetramer (HFPO)₄, 20 g (0.2 mol) of FSO₃H and 7 g (0.03 mol) of SbF₅ was refluxed for 40 h in a Teflon ® pot fitted with a Teflon ® water-cooled condenser connected to a Dry Ice-acetone cooled trap.

Water-cooling in the condenser was then stopped and the condenser was connected to a liquid nitrogen-cooled trap and vacuum of about 1 mm was applied while heating the pot until distillate was no longer condensing in the trap. Material in this trap and also in the Dry Ice-cooled trap was then transferred cold under vacuum to a liquid nitrogen-cooled still pot and distilled in a spinning band still with a water condenser connected to a Dry Ice-cooled trap.

CF₃CFHCOF (4.2 g), b p 26°, was recovered and characterized by infrared using a known sample of CF₃CFHCOF. Also recovered were about 21 g of CF₃CFHCOOCH₃, b p 93° to 100°; 111.5 g of (HFPO)₄ oligomer, b p 63°/22 mm; and 23 g of the methyl ester of (HFPO)₄, b p 43° to 49°/0.1 mm. The products were characterized by infrared and nmr.

EXAMPLE 7

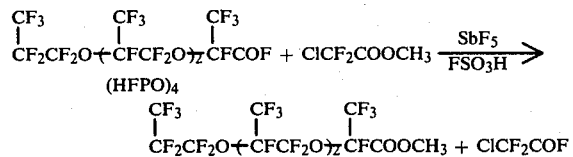

A mixture of 29 g (0.2 mol) of ClCF₂COOCH₃, 166 g (0.25 mol) of (HFPO)₄, 20 g (0.2 mol) of FSO₃H and 6.5 g of SbF₅ (0.03 mol) was refluxed for 15 h and worked up in the same manner as described for Example 6. The low-boiling condensate (12 g) comprising about 60% of ClCF₂COF, b p −27°, was characterized by infrared and nmr. Distillation of the material remaining in the reaction flask gave 6.5 g of the methyl ester of (HFPO)₄, 127 g of (HFPO)₄ and about 2 g of ClCF₂COOCH₃.

EXAMPLE 8

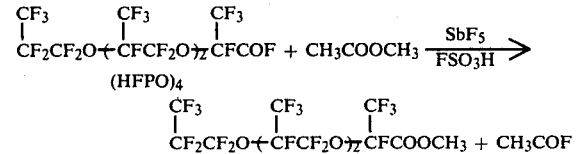

A mixture of 131 g (0.2 mol) of (HFPO)₄, 15 g (0.15 mol) of FSO₃H, 7 g (0.03 mol) of SbF₅ and 11 g (0.15 mol) of CH₃COOCH₃ was refluxed for 36 hours and worked up in the same manner as described for Example 6. There was isolated from the Dry Ice-cooled trap about 0.5 g of CH₃COF characterized by infrared and NMR. In addition, there was distilled 51 g of recovered (HFPO)₄ and 38 g of its methyl ester.

EXAMPLE 9

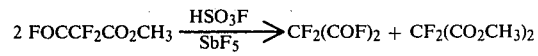

First, 829 g (5.31 mol) of FOCCF₂CO₂CH₃, 250 ml (4.35 mol) of fluorosulfonic acid and 25 ml (0.34 mol) and SbF₅ were mixed in a 1-liter Teflon ® flask attached to a Teflon ® reflux condenser. The reflux condenser was attached to a Dry Ice condenser which in turn delivered condensate to a Dry Ice-cooled receiver. Water was passed through the reflux condenser and the Teflon ® flask was warmed to 160° C. in an oil bath. The reaction was run 24 h and 238 g of product was collected in the receiver. This product was distilled to yield 208 g of perfluoromalonyl fluoride boiling at −6° to −4° C. Yield: 54%. Dimethyl difluoromalonate was also formed.

The embodiments of the invention in which an exclusive property or privilege is claimed are defined as follows:

1. A carboxylic ester/acyl fluoride interchange reaction process comprising the sequence:

$$RX\!-\!CO_2CH_3 + R'X'\!-\!COF \underset{}{\overset{catalyst}{\rightleftharpoons}} RX\!-\!COF + R'X'CO_2CH_3$$

wherein

X is methylene or substituted methylene selected from the group consisting of —CF₂—, —CFH—, —CFCl—, —CFBr—, —CFI—, and —C(CF₃)F—;

X' is substituted methylene selected from the group consisting of —CF₂—, —CFH—, —CFCl—, —CFBr—, —CFI—, and —C(CF₃)F—;

R and R' are the same or different and are selected from the group consisting of hydrogen, halogen, and halogen-substituted and unsubstituted alkyl, alkoxy, alkaryl, aralkyl, aryloxy and polyether alkyl of up to 18 carbon atoms;

R and X taken together can be R_FCOF;

R' and X' taken together can be R_FCO₂CH₃; and

R_F is a single bond or a linear or branched perfluoroalkylene group of up to 18 carbon atoms;

and wherein the catalyst is one or more metal fluorides selected from the group consisting of SbF₅, TaF₅, NbF₅, AsF₅, BiF₅, TiF₄, ZrF₄ and mixtures of SbF₅ and HF wherein HSbF₆ is present, and combinations of one or more of said metal fluorides with one or more strong sulfonic acids.

2. A process according to claim 1:

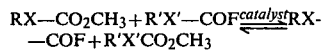

3. A process according to claim 1 wherein X is selected from the group consisting of —CF₂—, —CFH—, and —CFCl—; R is selected from the group consisting of hydrogen, fluorine, and perfluoroalkyl; X' is —CF₂— or —C(CF₃)F—; R' is CF₃CF₂CF₂O(CF(CF₃)CF₂O)_n wherein n is 0 to 10; R and X taken together are R_FCOF; R' and X' taken together are R_FCO₂CH₂; and R_F is —CF₂—.

4. A process according to claim 1, 2, or 3 wherein the strong sulfonic acid is selected from the group consisting of fluorosulfonic acid, trifluoromethane sulfonic acid and perfluorosulfonic acid resin.

5. A process according to claim 1 wherein R is —COF, X is —CF$_2$—, R' is CF$_3$CF$_2$CF$_2$O(CF(CF$_3$)CF$_2$O)—, and X' is —CF(CF$_3$)—.

6. A process according to claim 1 wherein R is CF$_3$, X is —CFH—, R' is CF$_3$CF$_2$CF$_2$O$\vphantom{.}$(CF(CF$_3$)CF$_2$O$\vphantom{.}$)$_2$, and X' is —CF(CF$_3$)—.

7. A process according to claim 1 wherein R is Cl, X is —CF$_2$—, R' is CF$_3$CF$_2$CF$_2$O(CF(CF$_3$)CF$_2$O)$_2$, and X' is —CF(CF$_3$)—.

8. A process according to claim 1 wherein R is H and X is —CH$_2$—, R' is CF$_3$CF$_2$CF$_2$O$\vphantom{.}$(CF(CF$_3$)CF$_2$O$\vphantom{.}$)$_2$, and X' is —CF(CF$_3$)—.

9. A process according to claim 2 wherein R$_F$ is —CF$_2$—.

10. A process according to claim 9 wherein the catalyst is a combination of fluorosulfonic acid and SbF$_5$.

* * * * *

UNITED STATES PATENT OFFICE
CERTIFICATE OF CORRECTION

PATENT NO. : 4,316,986
DATED : February 23, 1982
INVENTOR(S) : David Charles England, Robert Lee Kraft and Carl George Krespan It is certified that error appears in the above-identified patent and that said Letters Patent are hereby corrected as shown below:

In Claim 3, Column 6, line 63, "$R_FCO_2CH_2$" should read:

--$R_FCO_2CH_3$--.

In Claim 5, Column 7, lines 1 and 2, the expression, "R is -COF, X is -$CF_2$-" should be replaced by:

--R and X taken together are -$CF_2COF$--.

Signed and Sealed this

Twenty-fifth Day of October 1983

[SEAL]

Attest:

GERALD J. MOSSINGHOFF

Attesting Officer     Commissioner of Patents and Trademarks